United States Patent [19]

Ryback

[11] Patent Number: 4,771,476
[45] Date of Patent: Sep. 13, 1988

[54] SOUND CHAMBER CLOSURE FOR AN ELECTROACOUSTIC TRANSDUCER

[75] Inventor: Helmut Ryback, Langenzersdorf, Austria

[73] Assignee: AKG Alustische u.Kino-Geräte Gesellschaft mbH, Austria

[21] Appl. No.: 907,301

[22] Filed: Sep. 12, 1986

[30] Foreign Application Priority Data

Sep. 12, 1985 [AT] Austria ................................. 2670/85

[51] Int. Cl.$^4$ .......................... H04R 1/02; H04R 9/02; H01R 13/11; H01R 13/42
[52] U.S. Cl. ..................................... 381/154; 381/158; 381/194; 381/198; 381/199; 439/137; 439/852
[58] Field of Search ............... 381/154, 158, 192, 194, 381/198, 199, 201, 67; 181/137; 439/135–137, 852–853

[56] References Cited

U.S. PATENT DOCUMENTS

| | | | |
|---|---|---|---|
| 3,185,767 | 5/1975 | Olson et al. | 381/194 |
| 3,610,830 | 10/1971 | Daleiden | 381/123 |
| 4,028,491 | 6/1977 | Huntress | 381/123 |
| 4,234,766 | 11/1980 | Cacho | 381/194 |
| 4,395,589 | 7/1983 | Williams | 381/154 |

Primary Examiner—Jin F. Ng
Assistant Examiner—Danita R. Byrd
Attorney, Agent, or Firm—McGlew and Tuttle

[57] ABSTRACT

In a sound chaber closure for an electroacoustic transducer installed in a housing, in particular an electrodynamic sound generator with a moving coil, the housing is formed to receive a tubular acoustic plug with an acoustic line leading to a stethoscope earpiece. The acoustic plug can be introduced into a sound chamber of the housing which closes when the plug is being pulled out. To obtain a much better acoustic coupling of the stethoscope line to the sound generator, the sound chamber closure is designed as a slide which is arranged inclined on the axis of the sound exit opening designed as sound conduction tube, lies in the path of the connecting tubes of the acoustic plug to be inserted, and is integrally connected with a ring containing the transducer diaghragm with the moving coil, which ring abuts at the opening of a box-like housing, at the bottom of which is an annular gap magnet system, which ring is displaceable counter to the force of one or more springs perpendicular to the direction of introduction of the connecting tubes of the acoustic plug in the axial direction of the box-like housing, and that the moving coil is spaced from the magnet system, when the sound exit opening is closed by the slide, whereas with the acoustic plug introduced into the sound exit opening, it is in the air gap of the magnet system.

3 Claims, 1 Drawing Sheet

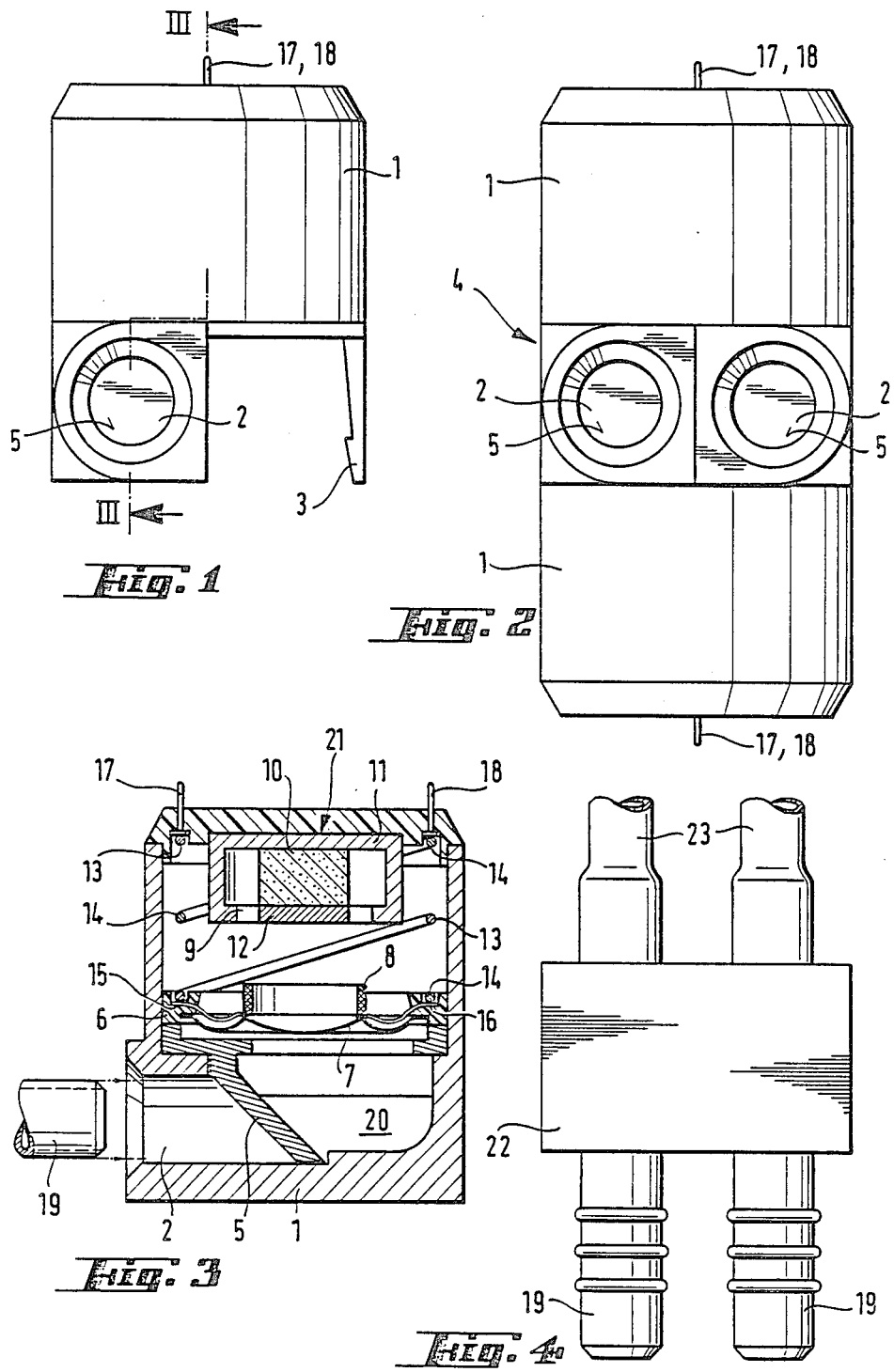

SOUND CHAMBER CLOSURE FOR AN ELECTROACOUSTIC TRANSDUCER

FIELD AND BACKGROUND OF THE INVENTION

This invention relates in general to sound devices and in particular to a new and useful sound chamber closure for an electro-acoustic transducer.

The invention relates to a sound or reverberation chamber closure for an electro-acoustic transducer installed in a housing, in particular an electrodynamic sound generator with a moving oil, which housing is designed to receive a tubular acoustic plug with an acoustic line leading to a stethoscope earpiece, which plug can be introduced into a sound chamber of the housing which closes as the acoustic plug is being pulled out.

A sound chamber closure of the above described kind has been described for example in U.S. Pat. No. 4,028,491. In the subject of this publication the closing occurs by means of a cylindrical jack which upon introduction of the acoustic plug is pushed axially inward into a tubular channel associated with the transducer housing counter to the pressure of a helical spring; and, in the inserted state, clears, via a relatively narrow bore, a sound path to the coupling space before the membrane of the sound generator, so that the sound radiated from the diaphragm can get to the acoustic plug and further via an acoustic line to the stethoscope earpiece. When the acoustic plug has been fully introduced, the last turn of the helical spring touches an electro-conducting, centered disk and an electro-conducting ring disposed concentric therewith and in this manner shortcircuits a resistor present in the circuit of the moving coil of the transducer.

The disadvantages of the known arrangement must be seen in that the sound exit opening is not sufficiently sealed against the penetration of dust and dirt particles into the coupling space and against the radiation of sound which could contribute to molesting the surroundings. Further, the small cross section of the sound path to the acoustic plug constitutes a coupling resistance between diaphragm and acoustic plug, which is not desirable because it causes losses in the sound conduction.

SUMMARY OF THE INVENTION

The invention provides an arrangement which does not have the disadvantages of the known sound chamber closure. According to the invention, a sound chamber closure is designed as a slide which is arranged inclined to the axis of the sound exit opening formed as a sound conduction tube and it lies in the path of the connection tube of the acoustic plug to be inserted. The sound closure is integrally connected with a ring containing the transducer diaphragm with the moving coil and the ring abuts at the opening of a box-like housing, on the bottom of which is an annular gap magnet system. The ring is displaceable counter to the force of one or more springs perpendicular to the direction of introduction of the connecting tubes of the acoustic plug in the axial direction of the box-like housing, and, when the sound exit opening is closed by the slide, the moving coil is spaced from the magnet system. When the acoustic plug is introduced into the sound exit opening, it is present in the air gap of the magnet system.

The advantage of the arrangement is that it has the greatest possible opening between the coupling space of the sound generator and the entrance opening of the acoustic plug. Thereby a much better acoustic coupling of the stethoscope line to the sound generator is given, because there are no additional chambers, formed by partitions, between the diaphragm of the sound generator and the acoustic plug. But also the continuous electric connection of the sound generator with the central station for the testing of the functionality of the sound generator in the program pauses is solved more simply in the invention, as it does not contain an electric switch and the moving coil of the transducer is always connected directly to the power supply line. Instead of the electric resistance, lying in the circuit of the moving coil of the transducer, for reducing the sound volume when the arrangement is not in use, in the invention the moving coil is moved out of the air gap of the magnet system, which movement results by release of the slide when the acoustic plug is being extracted from the tubular housing part. Due to the fact that the moving coil is then outside the magnetic field in the annular gap and is reached at most by the stray lines of force, the movement of the moving coil and hence of the diaphragm is so slight that no audible sound is generated. If, however, the moving coil is in the air gap of the magnet system, which state is obtained by introducing the acoustic plug into the tubular housing part, then the sound generator is acoustically active and the sound radiated from the diaphragm gets to the stethoscope earpiece practically unattenuated and hence with the full sound volume.

An advantageous realization of the sound chamber closure according to the invention is characterized in that the springs holding the slide and the diaphragm-carrying space from the magnet system are two helical springs which are offset relative to each other by 180° and form at least sections of electric connecting lines between the housing terminals and the terminals of the moving coil. This eliminates the need for separate leads to the moving coil, which because of the to-and-fro movement of the coil may easily lead to interruptions.

Accordingly it is the object of the invention to provide an improved sound chamber closure for an electro-acoustic transducer which is installed in a housing in particular for an electrodynamic sound generator with a moving coil, which comprises the housing which has a hollow interior with a tubular receptacle opening leading to an interior chamber in the housing with a deflector or wall closure in the inlet of the housing which is formed as a slide which is arranged inclined to the axis of the receiving opening and comprises a sound conduction tube which lies in the path of the connection tubes of the acoustic plug to be inserted.

Further object of the invention is to provide a sound chamber closure construction which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings,

FIG. 1 is a side elevational view of a housing provided with a sound chamber closure constructed in accordance with the invention;

FIG. 2 is a view similar to FIG. 1 indicating two housings plugged together for a two channel or stereo transmission;

FIG. 3 is a section taken along the line 3—3 of FIG. 1; and

FIG. 4 is a top view of an acoustic plug for a stereophonic earpiece used with the device of FIG. 1.

GENERAL DESCRIPTION OF THE PREFERRED EMBODIMENTS

Referring to the drawings in particular, the invention embodied therein comprises a sound chamber closure for an electro-acoustic transducer which is installed in a housing generally designated 1 and in particular to an electrodynamic sound generator with a moving coil wherein the housing is designed to receive a tubular acoustic plug 22 with an acoustic line 23 leading to a stethoscope earpiece.

FIG. 1 illustrates a housing 1 with a cylindrical sound exit opening 2 providing a sound conduction tube and receptacle for connection of the tubular acoustic plug 22 shown in FIG. 4. By means of the spring clip 3, two such housings 1 can be plugged together to form a two-channel or stereo unit. FIG. 2 shows such a two-channel or stereo unit 4. Inside the housing 1 are accommodated the electro-acoustic transducer, which is active as a sound generator, and the sound chamber closure.

An embodiment according to the invention is shown in FIG. 3 in transverse section through the housing 1. Inside the housing 1 is a deflectable sound chamber wall closure formed as a slide 5, which has a portion inclined to the axis of said sound receptacle opening and closes the cylindrical sound exit opening 2 off, soundproof against the coupling space 20 situated between the sound exit opening and an opening defined by wall portions of the housing in front of the diaphragm 7. The wall closure portions extends from an apertured disc portion abutting the wall portions of the housing defining the opening. When the cylindrical connecting tube 19 of the acoustic plug 22 is inserted into the sound exit opening 2, the slide 5 is displaced away from the opening, axially to the sound generator 21 counter to the force of the two springs 13, 14. Likewise the diaphragm-holding ring 6 carrying the diaphragm 7 and an annular gap magnet coil 8 is displaced axially from a position abutting the housing opening adjacent the coupling space 20 in the direction of the annular gap 9 of the magnet system consisting of magnet 10, pot magnet 11 and pole plate 12, so that in the end position, with the acoustic plug 22 fully introduced, coil 8 is immersed in the annular gap 9. The two springs 13 and 14 are electroconducting and establish a permanent electric connection between the terminals 17 and 18 on the outside of the housing 1 and the wire ends 15, 16 of the moving coil 8. The compression springs 13 and 14 are for this purpose arranged offset relative to each other by 180°, and their pitch is so high that even in the compressed state no contact of the individual turns takes place.

An acoustic plug 22 which establishes the acoustic connection to the stethoscope earpiece is shown in FIG. 4. It comprises the two cylindrical connecting tubes 19 and the flexible tube lines 23 propagating the sound.

While a specific embodiment of the invention has been shown and described in detail to illustrate the application of the principles of the invention, it will be understood that the invention may be embodied otherwise without departing from such principles.

What is claimed is:

1. An electroacoustic transducer device compising an electrodynamic sound generator with a moving coil installed in a housing having a hollow interior with a tubular receptacle opening into which a tubular acoustic plug with an acoustic line leading to a stethoscope earpiece can be inserted, said housing having a deflectable wall closure in said tubular receptacle which closes said opening as said acoustic plug is being withdrawn, said wall closure being formed as a slide which is arranged inclined to the longitudinal axis of said receptacle opening which comprises a sound conduction tube which lies in an insertion path of said acoustic plug; the sound generator comprising ring means carrying a transducer diaphragm having a moving coil located in said sound chamber adjacent an opening in the housing, and, an annular air gap magnet system fixed in the housing spaced from the opening, spring means acting against the ring means perpendicular to the insertion direction of said tubular acoustic plug and in the axial direction of said housing, to bias said moving coil away from the magnet system so that when the receptacle is closed by said slide the moving coil is spaced from the air gap, the wall closure being operatively connected to the ring means so that when the acoustic plug is inserted into the tubular receptacle opening to move the closure to an open condition the ring is urged by the wall closure against the action of the spring means towards the air gap magnet system to introduce the moving coil into the air gap of the magnet system.

2. An electroacoustic transducer device according to claim 1, wherein said spring means biasing said slide and said ring means carrying the diaphragm spaced from the magnet system include two helical springs which are offset relative to each other by 180° and form at least sections of electrical supply lines for the moving coil and for said magnet system, and form terminals extending out of said housing at the ends of said supply lines.

3. An electroacoustic transducer device comprising a housing providing an acoustic chamber and an electrodynamic sound generator in the chamber; the electrodynamic sound generator having an air gap magnet and a moving coil operatively carried by a transducer diaphragm unit and receivable in the air gap for operation of the sound generator; means mounting the transducer diaphragm unit for movement of the coil between positions remote from the air gap and within the air gap, respectively; the housing being formed with a socket for receiving an acoustic tube; a closure member for the socket mounted in the housing and operatively connected to the diaphragm unit; the closure member being mounted for movement by engagement with an acoustic tube inserted into the socket from a position closing the socket in which the moving coil is spaced from the air gap to an open position in which an acoustic tube is received in the socket and the moving coil is inserted into the air gap; resilient means in the housing biassing the closure member in the closed position, whereby insertion and removal of the acoustic tube into and out from the socket opens and closes the closure member inserting the coil into and removing the coil from the air gap respectively, to activate and deactivate the sound generating unit respectively.

* * * * *

UNITED STATES PATENT OFFICE
CERTIFICATE OF CORRECTION

Patent No. 4,771,476　　　　　　　　　Dated September 13, 1988

Inventor(s)　　　　Helmut Ryback

It is certified that error appears in the above-identified patent and that said Letters Patent is hereby corrected as shown below:

Title page:

Assignee's name is to be correctly spelled as:

AKG Akustische u.Kino-Geräte
    Gesellschaft m.b.H., Austria

In the first line of the ABSTRACT, change "chaber" to --chamber-

Signed and Sealed this

Fifth Day of September, 1989

Attest:

DONALD J. QUIGG

*Attesting Officer*　　　　*Commissioner of Patents and Trademarks*